United States Patent [19]
Hinks

[11] Patent Number: 4,579,531
[45] Date of Patent: Apr. 1, 1986

[54] DENTAL REPAIR APPARATUS HAVING A DENTAL ANCHORING DEVICE

[75] Inventor: Herbert N. Hinks, Brecon, Wales

[73] Assignee: Precision Dental Products Limited, London, England

[21] Appl. No.: 572,003

[22] Filed: Jan. 19, 1984

[30] Foreign Application Priority Data

Jan. 20, 1983 [GB] United Kingdom ................ 8301483

[51] Int. Cl.⁴ .............................................. A61C 5/04
[52] U.S. Cl. .................................... 433/225; 411/389
[58] Field of Search ....................... 433/225, 220, 221; 411/389, 412

[56] References Cited

U.S. PATENT DOCUMENTS 1,082,945 12/1913 Graham ............................... 411/389
4,219,620 8/1980 Carse .................................... 433/225
4,234,309 11/1980 Sellers .................................. 433/225

FOREIGN PATENT DOCUMENTS 76084 4/1983 European Pat. Off. ............ 433/225

Primary Examiner—John J. Wilson
Attorney, Agent, or Firm—Fleit, Jacobson, Cohn & Price

[57] ABSTRACT

A dental anchoring device including a stud, one end of which has a left hand external screw thread and the other end of which has a right hand external screw thread.

5 Claims, 4 Drawing Figures

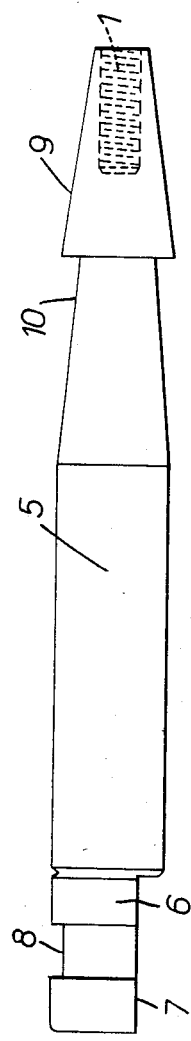
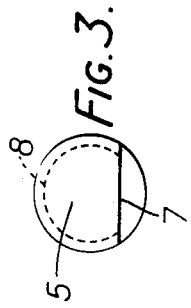
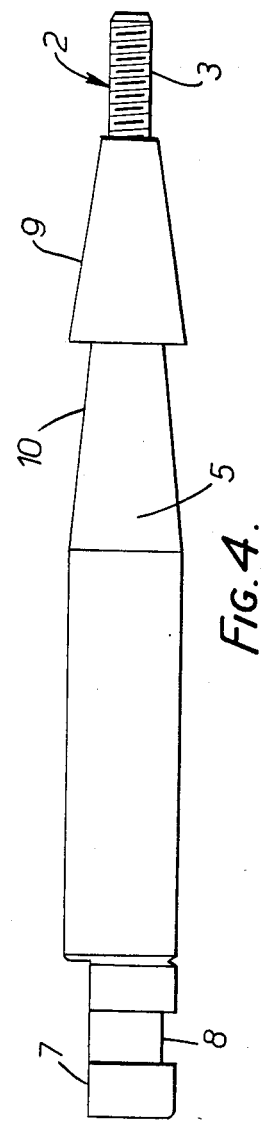
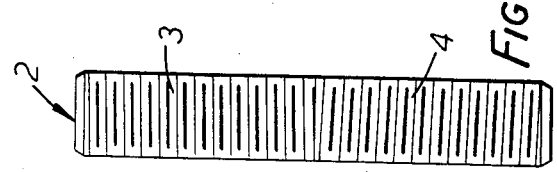

DENTAL REPAIR APPARATUS HAVING A DENTAL ANCHORING DEVICE

This invention relates to dental repair apparatus having a screw threaded dental anchoring device, the screw threaded dental anchoring device being for use in the anchoring of a replacement super structure to the under structure of a tooth.

In order to anchor a replacement super structure to the under structure of a tooth it is known to fit into the under structure a screw threaded anchoring device to serve as a tie which is effective to anchor the replacement super structure to the under structure.

One known device is fully described in U.K. Pat. No. 1482681 and comprises a threaded stud which is secured by means of a narrow neck portion to a shank which is adapted to be received by a dental hand piece. In use the stud, supported by the shank, is screwed into a prepared hole in the under structure of a tooth to be repaired, until it fills the hole. The narrow neck portion is then broken off consequent upon further rotation of the shank so as to leave a threaded portion of the stud projecting from the under structure to serve as an anchor for a replacement super structure. This known device may not always be successfully fitted since the weakened portion may either break prematurely, that is before the stud has been properly screwed into the hole, or it may not break as required when the hole has been filled by the stud and consequent upon further rotation of the stud, with the result that the thread in the under structure becomes stripped.

It is an object of the present invention to provide a dental repair apparatus in which the aforementioned disadvantages of known screw threaded anchoring devices are obviated or reduced.

According to the present invention a dental anchoring device includes a stud, one end portion of which has a left hand external screw thread and the other end portion of which has a right hand external screw thread.

The dental anchoring device may be a part of dental repair apparatus including a shank for supporting the stud, the shank having at one end thereof a screw threaded hole having threads of a hand which are complementary to the threads on one end of the stud and which at the other end thereof is adapted to be received into a dental hand piece, for example a latching type dental hand piece. The screw threaded hole will normally have left hand threads.

Thus in use, the stud supported in the shank, may be screwed home into a prepared hole in the under structure of a tooth to be repaired, until the hole is substantially filled with screw thread of one hand, such that resistance to rotation of the shank is encountered which will cause the shank to unscrew off the stud so that the stud is left screwed into the under structure.

The prepared hole may be tapped with a suitable complementary screw thread or alternatively the stud may be used to effect a self-tapping action as it is screwed into the hole.

The shank of the dental repair apparatus may have a first tapered portion adjacent the hole having the screw threads.

There may be provided a second tapered portion adjacent the first tapered portion.

The dental repair apparatus may include a drill which is suitable for providing a hole into which the stud can be screwed and which embodies a stop which determines the depth of the hole.

Although the shank may quite simply be loaded with a stud by a dentist or by a dental nurse just prior to a repair operation and reloaded as required, it is also contemplated that loaded shanks may be provided which may be discarded after use or which may be returned to the manufacturer to be reloaded.

One embodiment of the invention will now be described solely by way of example with reference to the accompanying drawings in which:

FIG. 1 is a side view of a dental anchoring device;

FIG. 2 is a side view of a shank of dental repair apparatus within which shank the dental anchoring device shown in FIG. 1 may be fitted;

FIG. 3 is an end view of the shank shown in FIG. 2; and

FIG. 4 is a side view of the shank shown in FIG. 2 and having a dental anchoring device supported therein.

Referring now to the drawings, a dental anchoring device comprises a stud 2, one end 3 of which is formed with a right hand external screw thread and the other end 4 of which is formed with a left hand external screw thread. The stud may be made of any suitable material such as stainless steel, gold, titanium or silver and the screw threads 3 and 4 may be formed by any known screw thread cutting process or by a press forming technique. The stud 2 shown in FIG. 1 may be supported by a shank 5 as shown in FIG. 2, one end 6 of which is suitably adapted to be received into a latching type dental hand piece. Latching type dental hand pieces are very well known and as can be seen from FIG. 2 and FIG. 3, the shank 5 is formed with a flat surface 7 and a circumferential groove 8 which match the latching mechanism of a standard latching dental hand piece. At the end of the shank 5 remote from the end 6, there is provided a tapped hole 1 which includes a left hand thread which is complementary to the thread formed on one end of the stud 2. Normally the hole 1 might be provided with a left hand screw thread and thus the part 4 of the stud 2 which projects from the shank 5 will be a right hand screw thread which is adapted to be self-tapped into a suitable recess in the under structure of a tooth to be repaired. In order to provide a dentist using the apparatus with an unobstructed view of the tooth under repair, one end of the shank 5 is provided with a taper 9 and a further taper 10 is provided to enable the shank 5 to be held conveniently by hand during a stud fixing operation.

In order to fit a stud such as the stud 2, a suitable hole is drilled in the under structure of a tooth to be repaired by using a drill which might embody a stop to determine hole depth and which is somewhat smaller than the outside diameter of the stud 2, such that the end 4 of the stud 2 can be self-tapped into the hole in the under structure of a tooth to be repaired. When the hole has been filled by the end 4 of the stud 2, resistance to rotation will be felt which will be sufficient to cause the left hand thread of the stud to unscrew progressively from the hole 1 in the shank 5 so as to leave the stud 2 firmly screwed into the under structure. The stud 2 may be treated during manufacture so that the end 4 which is arranged to self-tap into the under structure 2 of a tooth is hard enough to afford a self-tapping action and the end 3 of the stud 2 is annealed whereby if necessary it may be bent so as to facilitate anchorage of a replacement super structure.

The shank 5 may be manufactured from various materials such for example as surgical stainless steel. The shank may also be manufactured from aluminium and anodised for size colour coding.

The shank 5 may be disposable or it may be returned to a factory to be reloaded. At the factory, a stud 2 can be inserted into the shank 5 with the required measured amount of torque.

Various modifications may be made to the arrangement shown without departing from the scope of the invention and for example the threaded portions 3 and 4 of the stud 2 may not occupy the whole length of the stud, and although in the arrangement shown the shank is provided with two tapered portions 9 and 10, other alternative configurations may be provided.

I claim:

1. A dental repair apparatus comprising a dental anchoring device and a shank for supporting the dental anchoring device, the dental anchoring device comprising a stud, one end portion of which has a left hand external screw thread and the other end portion of which has a right hand external screw thread, and the shank having at one end thereof a hole for receiving one end of the stud and which at the other end thereof is adapted to be received into a dental handpiece, said one end of said stud being removably threaded in the hole of said shank.

2. Dental repair apparatus as claimed in claim 1 wherein the shank is adapted at the said other end thereof to be received into a latching type dental handpiece.

3. Dental repair apparatus as claimed in claim 2 wherein the shank has a first tapered portion adjacent said hole.

4. Dental repair apparatus as claimed in claim 3 wherein the shank is provided with a second tapered portion adjacent the first tapered portion.

5. Dental repair apparatus as claimed in claim 4 and including a drill which is suitable for providing a hole into which the stud can be screwed and which embodies a stop which determines the depth of the hole.

* * * * *